(12) United States Patent
Santelli, Jr.

(10) Patent No.: US 9,259,501 B2
(45) Date of Patent: Feb. 16, 2016

(54) ANTIMICROBIAL NASAL INSERT AND METHOD OF MANUFACTURING

(71) Applicant: Al Santelli, Jr., Martinsville, NJ (US)

(72) Inventor: Al Santelli, Jr., Martinsville, NJ (US)

( * ) Notice: Subject to any disclaimer, the term of this patent is extended or adjusted under 35 U.S.C. 154(b) by 40 days.

(21) Appl. No.: 13/835,811

(22) Filed: Mar. 15, 2013

(65) Prior Publication Data

US 2014/0261459 A1    Sep. 18, 2014

(51) Int. Cl.
| | |
|---|---|
| *A62B 23/06* | (2006.01) |
| *A61K 9/00* | (2006.01) |
| *A61L 9/16* | (2006.01) |
| *A61K 33/38* | (2006.01) |
| *A61L 2/00* | (2006.01) |
| *A61L 2/238* | (2006.01) |
| *A61F 5/08* | (2006.01) |

(52) U.S. Cl.
CPC ................ *A61L 9/16* (2013.01); *A61K 9/0043* (2013.01); *A61K 33/38* (2013.01); *A61L 2/0082* (2013.01); *A61L 2/238* (2013.01); *A62B 23/06* (2013.01); *A61F 5/08* (2013.01)

(58) Field of Classification Search
CPC ............. A61F 5/08; A61F 5/56; A62B 23/06; A61K 9/00; A61K 9/0012; A61K 9/0043
USPC .......... 128/848, 858, 200.26, 204.12, 206.11, 128/207.18; 606/199; 424/422, 423, 434, 424/443, 445, 447
See application file for complete search history.

(56) References Cited

U.S. PATENT DOCUMENTS

| | | | | |
|---|---|---|---|---|
| 4,592,357 | A * | 6/1986 | Ersek ............................ | 606/199 |
| 8,048,102 | B2 * | 11/2011 | Thomas ........................ | 606/199 |
| 2004/0154626 | A1 * | 8/2004 | Washburn et al. ............ | 128/861 |
| 2009/0250067 | A1 * | 10/2009 | Beck Arnon ............ | 128/207.18 |
| 2010/0291169 | A1 * | 11/2010 | Toreki ............... | A61F 13/00063 424/405 |
| 2012/0060842 | A1 * | 3/2012 | Curtis ...................... | 128/206.11 |
| 2012/0330345 | A1 * | 12/2012 | Tasca ........................... | 606/199 |

\* cited by examiner

*Primary Examiner* — Alireza Nia
*Assistant Examiner* — Keri J Nelson
(74) *Attorney, Agent, or Firm* — Porzio, Bromberg & Newman, P.C.

(57) ABSTRACT

A nasal insert including an antimicrobial agent is inserted into the nose to eliminate or reduce undesirable microbes in the area just inside the nose. Pads of the nasal insert can be formed from a blended polymer compound with a microbial agent. Processing of the pre-polymer results in the microbial agent being trapped in the polymer. A blowing agent or $CO_2$ gas can be introduced in the process after decompression, and before molding to improve attraction of liquid born microbes to the nasal insert.

14 Claims, 6 Drawing Sheets

ANTIMICROBIAL NASAL INSERT AND METHOD OF MANUFACTURING

BACKGROUND OF THE INVENTION

1. Field of the Invention

The present invention relates to a nasal insert formed of a plastic material blended with an antimicrobial agent and a method of making the nasal insert to improve attraction of microbes to the nasal insert, and allow for maximum contact of the nasal insert with the host environment.

2. Description of Related Art

Medical devices incorporating antimicrobial agents are known. U.S. Pat. No. 5,326,567 describes antimicrobial agents as chemical compositions that inhibit microbial growth or kill bacteria, fungi and other microorganisms. A liquid silver-based antimicrobial composition is formed of a stabilizing acyclic polyether polymer, silver ion and a stabilizing halide. The composition can be applied to the medical device through painting spraying or dipping to all surfaces.

U.S. Patent Application Publication No. 2012/0067346 describes a strip or mask for reducing spread of bacterial infections such as methicillin-resistant *staphylococcus aureus* (MRSA). The strip or mask contains an antimicrobial agent capable of being delivered to eradicate the colonization of bacteria within the nose. The strip is applied to the nose or a surgical mask is placed over the nose and mouth. In one embodiment, the strip or mask may contain a plurality of layers having a silver coating or a compound containing silver which reacts with skin or moisture to release silver to the colony in the nose.

It is desirable to provide an improved medical device in which all surfaces of the device include antimicrobial properties for attracting microbes, such as bacteria, and releasing antimicrobial agents for killing or inhibiting the growth of the microbes.

SUMMARY OF THE INVENTION

The present invention relates to a nasal insert including an antimicrobial agent to create an antimicrobial device. The nasal insert is inserted into the nose to eliminate or reduce undesirable microbes in the area just inside the nose. It is believed that certain microbes such as methicillin-resistant *staphylococcus aureus* (MRSA) colonize in the nose, and the nasal insert can be effective in treating or eliminating the colony of bacteria in the nose.

The nasal insert can include two or more contact pads attached to one another by a spring joiner. The joiner creates tension that applies pressure to the pads. An insertion tab is removably coupled to the spring joiner. The nasal insert is inserted in the nose by grasping the insertion tab. After insertion of the nasal insert, the insertion tab can be removed from the spring joiner. Upon insertion of the nasal insert, the pads contact an area of the inner nostril. The nasal insert can be removed from the nose by grasping of the joiner.

The pads of the nasal insert can be formed from a blended polymer compound with a microbial agent. Processing of the blended polymer compound results in the microbial agent being trapped in the polymer. In one embodiment, the microbial agent is silver which is blended into nylon (polyamide). The blended polymer compound can be injection molded into the shape of the nasal insert. When the formed nasal insert comes in contact with other materials such as human skin and or sensitive tissue, the microbial agent entrapped in the polymer has minimal contact with the application. This provides the nasal insert with a non-leaching property of the microbial agent.

A blowing agent or $CO_2$ gas can be introduced in the process after decompression, and before molding. The gas provides at least three basic product functions. The first function is to reduce the density of the polymer. The second function is to provide space for the microbial agent to naturally react with the host environment. The microbial agent can react to its environment naturally releasing ions, yet not leave the polymer structure. The third function pertains to voids created in the molded product by the gas after cooling of the polymer. The internal voids increase internal surfaces of the polymer allowing more of the antimicrobial agent to react throughout the polymer structure than it would naturally.

During molding of the nasal insert, texturing and surface wave details can be formed on the outer surface of the pads to allow the product the ability to maximize contact with the host environment by increasing the surface area of the pads. Application of the surface texture increases attraction and retention of microbes to the nasal insert from the host environment by capillary action. Surface treatments can be applied to the nasal insert for increasing the surface tension thereby aiding in the adhesion of microbes during use of the nasal insert. The surface treatments can be applied by means of flame or corona treatment of the surface of the nasal insert.

The absorptive properties of the nasal insert allow the product the potential to draw liquid born microbes to the nasal insert, and allow for maximum contact with the host environment. The absorption can also hold to the surface various mechanically detached particulates as further reinforcement to the non-leaching properties.

The invention will be more fully described by reference to the following drawings.

BRIEF DESCRIPTION OF THE DRAWINGS

FIG. 1A is a schematic diagram of a nasal insert including a pair of pads connected by a joiner.

FIG. 1B is a top plan view of FIG. 1A.

FIG. 1C is a side elevational view of FIG. 1A.

FIG. 2 is a schematic diagram of a tab used with the nasal insert shown in FIG. 1A.

FIG. 3A is a schematic diagram of a nasal insert including a wave pattern.

FIG. 3B is a top plan view of FIG. 3A.

FIG. 3C is a side elevational view of FIG. 3A.

FIG. 4 a schematic diagram of a nasal insert including four pads in which two pairs of the pads are connected by a micro-joiner and each pair of pads are connected to each other with a joiner.

FIG. 5A is a plan view schematic diagram of the nasal insert shown in FIG. 4.

FIG. 5B is a side elevational view of FIG. 4.

FIG. 6 a schematic diagram of a nasal insert including a multiple pad tube.

FIG. 7 is a plan view of the nasal insert shown in FIG. 6.

FIG. 8 is a flow diagram of a method of forming a nasal insert.

DETAILED DESCRIPTION

Reference will now be made in greater detail to a preferred embodiment of the invention, an example of which is illustrated in the accompanying drawings. Wherever possible, the same reference numerals will be used throughout the drawings and the description to refer to the same or like parts.

Figure 1A:
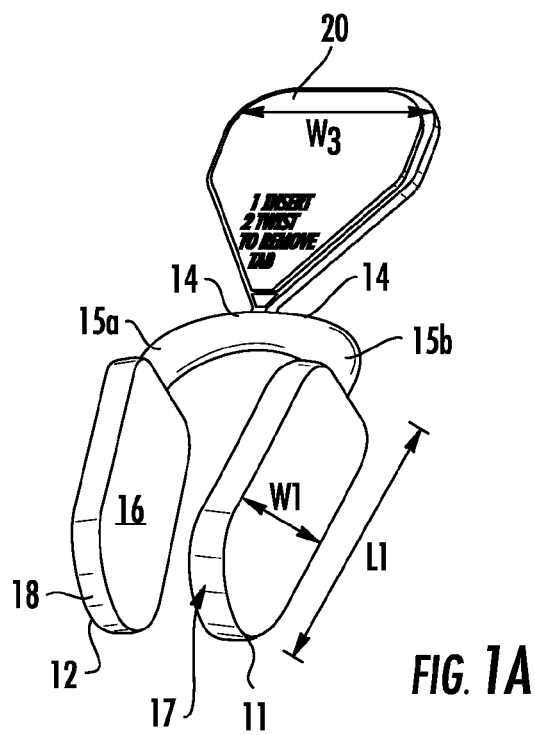
Figure 1B:
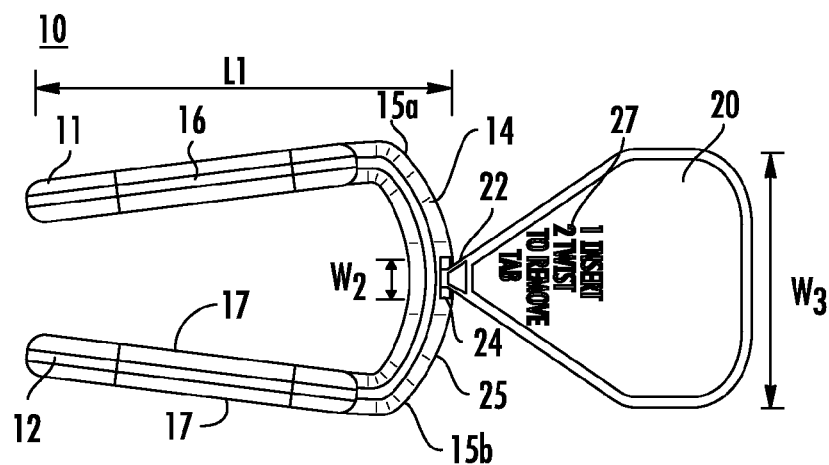
Figure 1C:
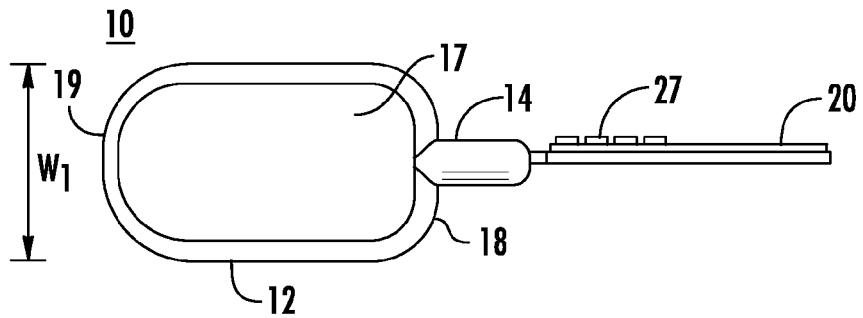

FIGS. 1A-1C illustrates nasal insert 10 in accordance with the teachings of the present invention. Nasal insert 10 includes pads 11, 12. Joiner 14 connects pads 11, 12 in a spaced apart relation to form a clip. End 15a of joiner 14 is coupled to pad 11 and end 15b of joiner 14 is coupled to pad 12.

Surface 16 of pad 11 and surface 17 of pad 12 can be a textured surface. For example, surface 16 and surface 17 can include a plurality of micro-pores extending into surface 16 and surface 17 to create the textured surface. The textured surface can have a depth up to about 0.0015 inches. Length $L_1$ of pad 11 and pad 12 can be longer than width $W_1$ of pad 11 and pad 12 to form an elongated pad. Upper edge 18 of pad 11 and pad 12 and lower edge 19 of pad 11 and pad 12 can be rounded. The smooth contours and rounded edges of pad 11 and pad 12 allow for comfortable insertion, increased long wear comfort as well as increased surface area.

Pads 11, 12 can be formed of a plastic material comprising an antimicrobial agent. The plastic can be a rigid plastic. For example, pads 11, 12 can be formed of nylon and in particular a synthetic polyamide polymer. The antimicrobial agent is blended into a plastic pre-polymer before molding of the plastic material into pads 11, 12. Suitable antimicrobial agents are metal antimicrobial agents including silver, gold, platinum, copper, zinc or palladium. The antimicrobial agents can include metal cations. The preferred metal ion is silver ion. The antimicrobial agent can be provided in an effective amount capable of interacting with a colony of microbes for suppressing colonization or killing of the colony. Example microbes include bacteria of methicillin-resistant *staphylococcus aureus* (MRSA).

Figure 2:
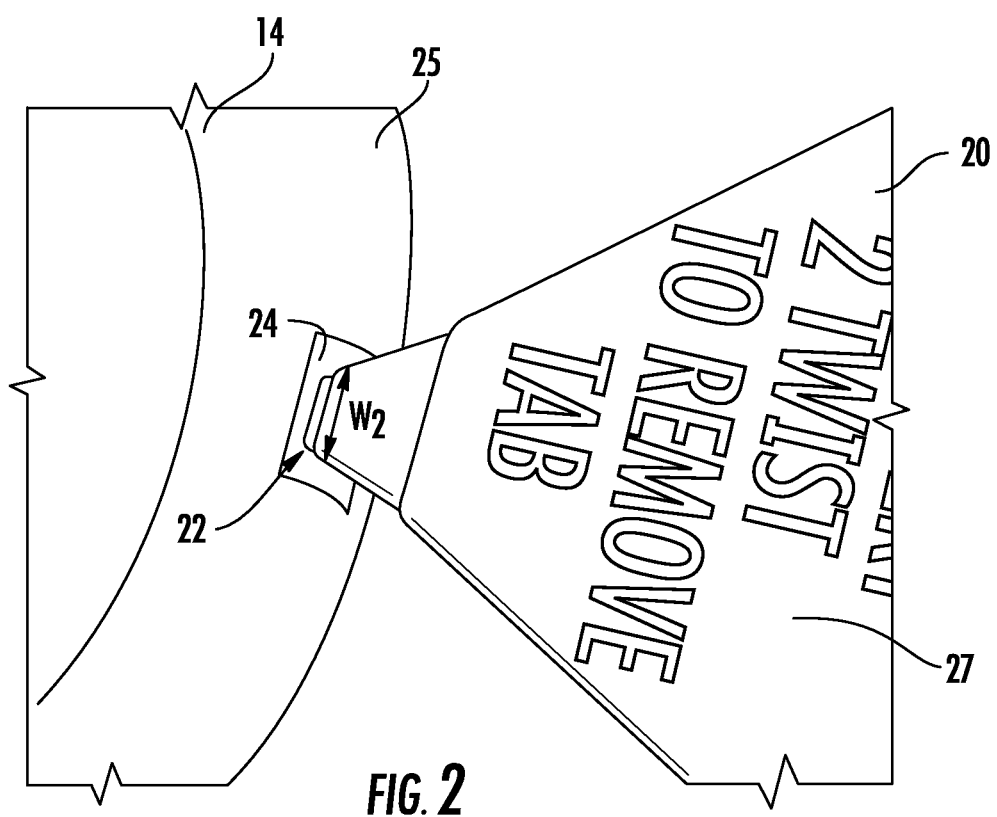

Insertion tab 20 is removably coupled to joiner 14, as shown in FIG. 2. In one embodiment, insertion tab 20 includes frangible detail 22. Frangible detail 22 has a width $W_2$ which is smaller than width $W_3$ of insertion tab 20, as shown in FIG. 1. Width $W_3$ is selected to provide a surface which can be grasped by a user during insertion of nasal insert 10. Width $W_2$ is selected to allow insertion tab 20 to be removed from joiner 14 by twisting of insertion tab 20 to break frangible detail 22. Frangible detail 22 can be attached within recess 24 on top 25 of joiner 14. Frangible detail 22 is recessed into recess 24 to allow any detachment burrs from the removal of insertion tab 20 to extend within recess 24 and below top 25 of joiner 14. Area 27 of insertion tab 20 can be used for printing indicia of product identification. Insertion tab 20 provides a point of insertion of nasal insert 10 away from the user portion of insert nasal insert 10 including pads 11, 12.

Joiner 14 can be formed of a flexible material to bias pad 11 and pad 12 for allowing pads 11 and 12 to remain in contact with the inner nostril upon insertion of pads 11 and 12 into the nose. For example, joiner 14 can be formed of a thermoplastic material. A suitable thermoplastic material is polyurethane. Alternatively, joiner 14 can be integral with pads 11, 12. Joiner 14 and pads 11, 12 can be formed of rigid plastic.

The thickness of joiner 14 can be adjusted to control the pressure exerted outwardly by pads 11, 12. For example, joiner 14 can have a thickness in the range of about 0.05 inches to about 0.110 inches. Joiner 14 can have a curved shape. The curve of joiner 14 allows for variation in nose shape relieving pressure on the underside of the nose, and provides increased comfort for the wearer upon insertion of pads 11 and 12 into the nose. The narrow width of joiner 14 provides a discreet appearance of nasal insert 10 when in use.

A colorant can be added to the plastic material for nasal insert 10. For example, the colorant can have a flesh tone to allow a cosmetic blend of nasal insert 10 to a user's skin and provide a less noticeable appearance.

Figure 3A:
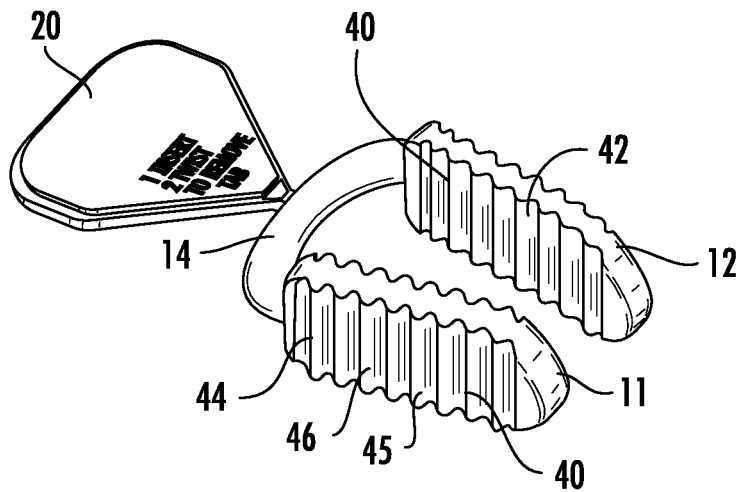
Figure 3B:
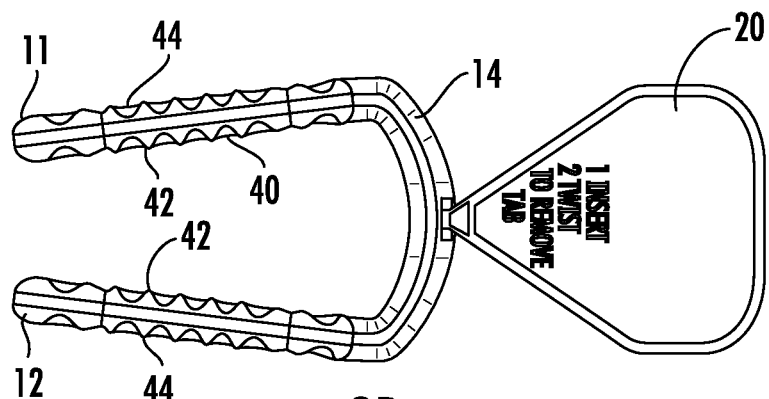
Figure 3C:
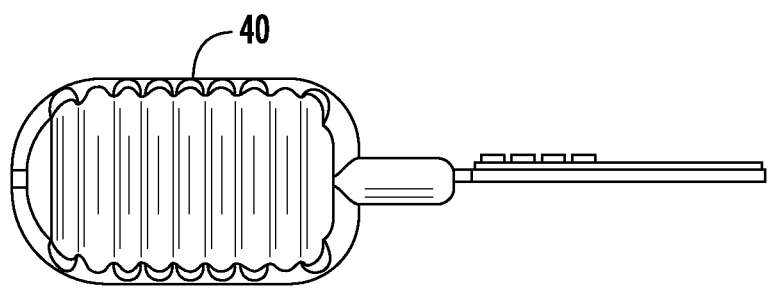

In one embodiment, pad 11 and pad 12 can include a surface wave 40 on one or both of inner surface 42 and outer surface 44 as shown in FIGS. 3A-3C. Surface wave 40 comprises a plurality of ridges 45. Surface wave 40 can increase the surface area of pads 11 and 12 up to about 50%.

Figure 4:
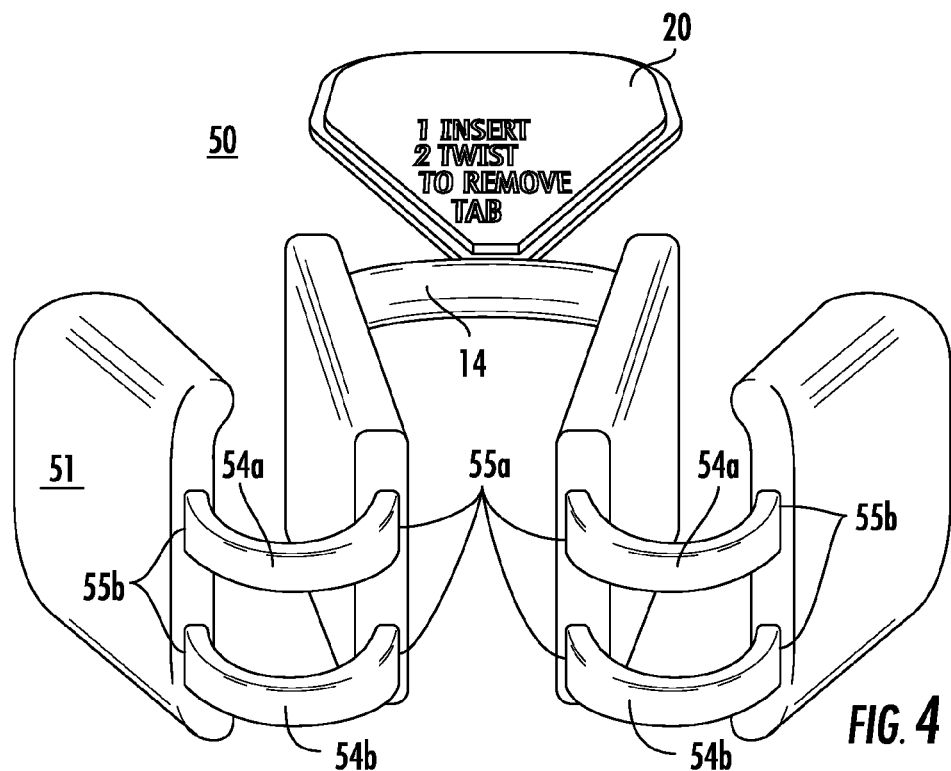
Figure 5A:
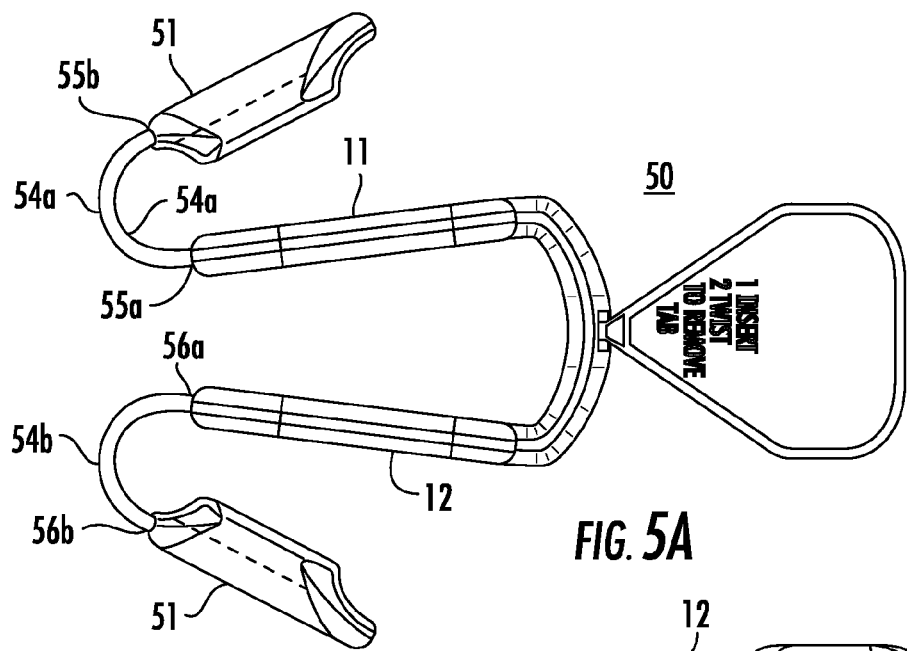
Figure 5B:
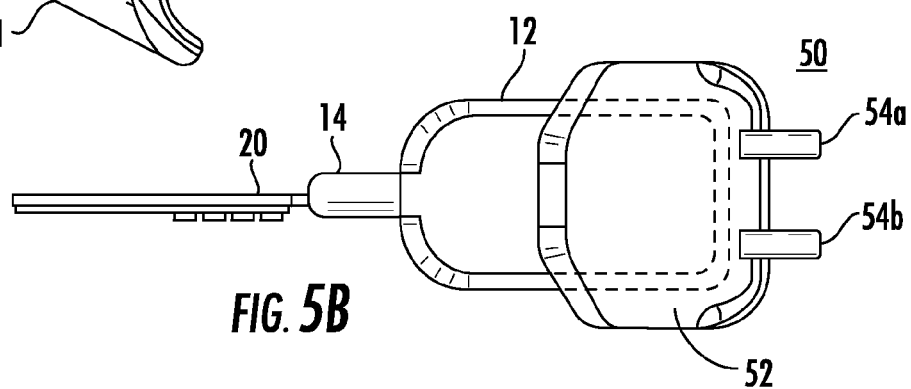

FIGS. 4 and 5A and 5B, illustrate an alternate embodiment of nasal insert 50 including a double clip. Micro-joiner 54a connects pad 11 to pad 51 in a spaced apart relation. End 55a of micro-joiner 54a is coupled to pad 11 and end 55b of micro-joiner 54a is coupled to pad 51. Micro-joiner 54b connects pad 12 to pad 52 in a spaced apart relation. End 56a of micro-joiner 54b is coupled to pad 12 and end 56b of micro-joiner 54b is coupled to pad 52. A pair of micro-joiners 54a and 54b can be used to connect respective pad 11 to pad 51 and pad 21 to pad 52.

Micro-joiners 54a and 54b can be formed of a flexible material to bias respective pads 11 and 51 and pads 12 and 52 for allowing the pads to remain in contact with the inner nostril upon insertion of the pads into the nose. The thickness of micro-joiners 54a, 54b can be adjusted to control the pressure exerted by pads 11, 12, 51 and 52. For example, micro-joiner 54a, 54b can have a thickness in the range of about 0.025 inches to about 0.050 inches. Micro-joiners 54a, 54b can have a curved shape.

In one embodiment, nasal insert 50 is formed of a thermoplastic material. A suitable thermoplastic material is polyurethane having about 80 durometer. Alternatively, pads 11, 12, 51 and 52 can be formed of a rigid plastic material, such as nylon. A flexible plastic material can be co-molded, over molded or insert molded with the plastic material. The co-molded flexible plastic material can be used to form joiner 14 and micro-joiners 54a, 54b. The co-molded plastic material can be a thermoplastic material.

Figure 6:
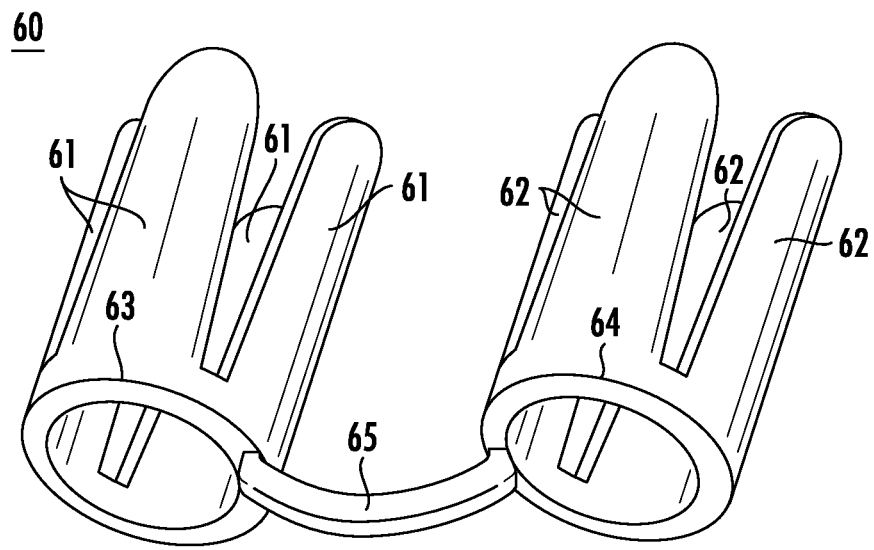
Figure 7:
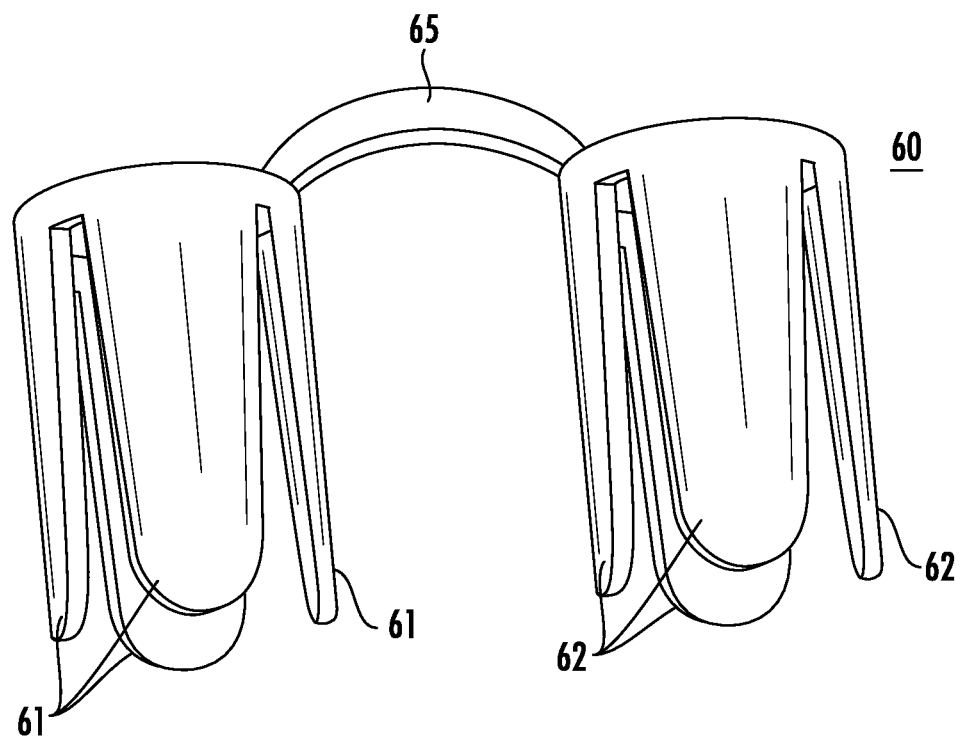

FIGS. 6 and 7 illustrate an alternate embodiment of nasal insert 60 including a multiple pad tube. A plurality of pads 61 extend from ring 63 and a plurality of pads 62 extend from ring 64. For example, four pads 61 can extend from ring 63 and four pads 62 can extend from ring 64. Joiner 65 connects ring 63 to ring 64 in a spaced apart relation. End 66a of joiner 65 is coupled to ring 63 and end 66b of joiner 65 is coupled to ring 64. Pads 61 can be integral with ring 63 and pads 62 can be integral with ring 64. Joiner 65 can be integral with ring 63 and ring 64. In one embodiment, nasal insert 60 is formed of flexible polyurethane having about 60 durometer.

Nasal inserts 10, 50 and 60 can be formed of a plastic and/or thermoplastic material including one or more additives. The additives can include antimicrobial agents. Preferably, the antimicrobial agent is silver. Alternative antimicrobial agents include copper or any other known antimicrobial agent capable of delivery from nasal inserts 10, 50 and 60. The additives can be blended into a base material for entrapping the additives throughout nasal inserts 10, 50 and 60.

Figure 8:
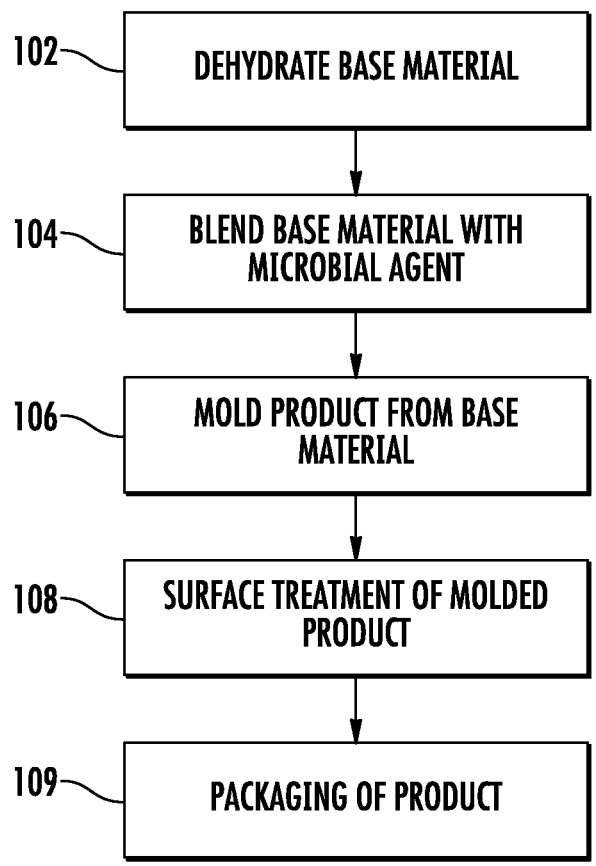

A method for manufacturing nasal insert 10, 50 and 60 having improved release of the entrapped microbial agents and attraction of microbes is shown in FIG. 8.

In block 102, a base material is dehydrated. The base material is selected to be a hydroscopic material for increasing the performance of the microbial agent. The base material can be dehydrated using conventional methods including drying in an oven, forced hot air or desiccant drying. Preferably, the base material is a pre-polymer plastic, for example nylon or a thermoplastic material, such as polyurethane. The base material is preferably a material that absorbs moisture for providing a maximum breakdown of the microbial agent, and allowing for the release of the microbial agents from the base material to affect microbes.

In block 104, the dehydrated base material is blended with a microbial agent. Preferably, during the blending step of block 104 the density of the base material is reduced. The density of the dehydrated base material can be reduced by blending the base material with a blowing agent or an injection of carbon dioxide gas into the base material creating a foaming effect. The foaming effect causes the base material to become porous and results in a decrease in density. The decrease in density allows for subatomic particles of the microbial agent to move more freely throughout the compound. The porosity also provides space for receiving moisture. The moisture can react with the microbial agent for accelerating the breakdown of the microbial agent thus increasing release of ions of the microbial agent from the base material. Example blowing agents include calcium carbonate and blowing agents manufactured by Reedy International as RCP40. The blowing agent can be added in an amount in the range of about 1% to about 3% by weight of the base material.

Example suitable microbial agents include silver, silver nano-particles, additives of silver such as are manufactured by Biomaster Antimicrobial Technology. The amount of the microbial agent used can be selected to increase the dielectric constant of the base material not to exceed the percolation threshold of the base material. An increased dielectric constant attracts negatively charged microbes providing improved ability of the base material to attract the microbes. The amount of microbial agent can be in the range of about 1% to about 25%.

The base material, such as a pre-polymer compound is blended with the microbial agent using heat and high compression mixing simultaneously, thereby causing the microbial agent to be evenly distributed throughout the polymer compound. Blending in this manner retains the microbial agent between the polymer strand structures. The base material can blended at a temperature in the range of about 350 degrees F. to about 475 degrees F. at a pressure in the range of about 0 to about 1500 psi.

In block 106, the blended base material is molded by injection molding to form nasal insert 10, nasal insert 50 or nasal insert 60. During block 106, a flexible plastic material can be co-molded with the base material for forming joiner 14 and micro-joiners 54a, 54b as described above. The cavity used in the injection mold can be selected to be larger than the desired product for providing pressure reduction and voids in the formed product to achieve a reduced density of the product. The cavity used in the injection mold can have a runout area allowing for a pressure drop, to maximize the foaming action and providing a pressure reduction and voids in the formed product to achieve a reduced density of the product.

In block 108, the molded product of the nasal insert is surface treated to raise the surface tension that holds microbes to the nasal insert. For example, the molded nasal insert can be flame treated or treated with corona discharge. The surface treatment of nasal insert 10, 50 improves retention of microbes on nasal insert 10, 50 or 60.

Surface treatment can also include silk screening and sputter coating of a biologically active or electrically active agent. Surface treatment can also include hydrophilization spot coating to enhance the capability to absorb and retain moisture.

Steps 104-108 are performed in a moisture free environment. In block 109, the molded product is packaged in a UV and moisture proof package. When the package is opened for use, the nasal insert will begin to absorb moisture to about 0.2% to about 0.8% equilibrium and then continue to absorb moisture to about 1.6% saturation during use of the nasal insert.

It is to be understood that the above-described embodiments are illustrative of only a few of the many possible specific embodiments, which can represent applications of the principles of the invention. Numerous and varied other arrangements can be readily devised in accordance with these principles by those skilled in the art without departing from the spirit and scope of the invention.

What is claimed is:

1. A nasal insert comprising;
   a pair of first pads, and
   a joiner connecting said first pads in a spaced apart relation, wherein said first pads are formed of a blend of a pre-polymer plastic material and an antimicrobial agent to distribute the antimicrobial agent throughout the pre-polymer plastic material, the pre-polymer plastic material is nylon or polyurethane and the nasal insert is formed in an injection molding process with a blowing agent or gas introduced to the blend before the injection molding process to cause a foaming effect in the blend to form internal voids in the nasal insert during the injection molding process and reduce the density of the pre-polymer plastic material allowing for ion movement of said antimicrobial agent which is trapped in polymer strands of the nasal insert formed during the injection molding process, the trapped antimicrobial agent is adapted to attract liquid born microbes to the nasal insert.

2. The nasal insert of claim 1 wherein each of said first pads have a length which is longer than the width to form an elongated pad.

3. The nasal insert of claim 1 where in said nylon is synthetic polyamide polymer.

4. The nasal insert of claim 3 wherein said antimicrobial agent is a silver cation.

5. The nasal insert of claim 1 wherein said joiner is formed of a flexible plastic material to bias said first pads.

6. The nasal insert of claim 1 wherein texture is formed on a surface of the first pads.

7. The nasal insert of claim 1 wherein a surface wave is formed on an inner and/or an outer surface of the first pads, the surface wave comprising a plurality of ridges.

8. The nasal insert of claim 1 further comprising:
   an insertion tab removably coupled to the joiner, said insertion tab including a frangible detail having a width smaller than the width of the insertion tab.

9. The nasal insert of claim 8 wherein said detail is attached within a recess in a top of said joiner.

10. The nasal insert of claim 1 wherein said joiner has a curved shape.

11. The nasal insert of claim 1 further comprising a colorant.

12. The nasal insert of claim 1 further comprising:
   a second pad connected to one of said first pads with a first micro-joiner and a third pad connected to the other one of said first pads with a second micro-joiner.

13. The nasal insert of claim 12 wherein said first and second micro-joiners are formed of a thermoplastic material.

14. The nasal insert of claim 12 wherein said second and third pads are formed of a plastic material co-molded, over molded or insert molded with a thermoplastic material forming said joiner and said micro-joiners.

* * * * *